US009761335B2

(12) United States Patent
Prible et al.

(10) Patent No.: US 9,761,335 B2
(45) Date of Patent: Sep. 12, 2017

(54) METHOD FOR MONITORING BORON DILUTION DURING A REACTOR OUTAGE

(71) Applicant: Westinghouse Electric Company LLC, Cranberry Township, PA (US)

(72) Inventors: Michael C. Prible, Pittsburgh, PA (US); Andrew M. Bunker, Pittsburgh, PA (US); Michael D. Heibel, Harrison City, PA (US)

(73) Assignee: Westinghouse Electric Company LLC, Cranberry Township, PA (US)

( * ) Notice: Subject to any disclaimer, the term of this patent is extended or adjusted under 35 U.S.C. 154(b) by 1169 days.

(21) Appl. No.: 14/058,324

(22) Filed: Oct. 21, 2013

(65) Prior Publication Data

US 2015/0110235 A1    Apr. 23, 2015

(51) Int. Cl.
| | |
|---|---|
| G21C 17/00 | (2006.01) |
| G21C 17/022 | (2006.01) |
| G01N 23/09 | (2006.01) |
| G21C 17/108 | (2006.01) |
| G21C 17/112 | (2006.01) |

(52) U.S. Cl.
CPC ........... *G21C 17/022* (2013.01); *G01N 23/09* (2013.01); *G21C 17/108* (2013.01); *G21C 17/112* (2013.01)

(58) Field of Classification Search
CPC ........ G21C 17/00; G21C 17/02; G21C 17/06; G21C 17/063; G21C 17/10; G21C 17/104; G21C 17/112
See application file for complete search history.

(56) References Cited

U.S. PATENT DOCUMENTS

| | | | |
|---|---|---|---|
| 6,345,080 B1 | 2/2002 | Bauer et al. | |
| 7,894,565 B2 | 2/2011 | Heibel et al. | |
| 2004/0101082 A1 | 5/2004 | Chao et al. | |
| 2010/0150295 A1 | 6/2010 | Heibel et al. | |
| 2012/0219101 A1* | 8/2012 | L'Abbate | G21C 7/00 376/215 |

FOREIGN PATENT DOCUMENTS

| | | |
|---|---|---|
| CN | 102 376 374 A | 3/2012 |
| JP | H02 242197 A | 9/1990 |
| JP | 2001502801 A | 2/2001 |
| JP | 2009150838 A | 7/2009 |

OTHER PUBLICATIONS

International Search Report and Written Opinion of the International Searching Authority for PCT/US2014/051423 dated Dec. 8, 2014 (Forms PCT/ISA/220, PCT/ISA/210, PCT/ISA/237).
14856279.6-1556/3061100 PCT/US2014051423—Extended European search report, including supplementary European Search Report and European search opinion (Forms 1507S, 1503, P0459, P04A42, 1703).

* cited by examiner

*Primary Examiner* — Marshall O'Connor
(74) *Attorney, Agent, or Firm* — Eckert Seamans Cherin & Mellott, LLC; Daniel C. Abeles

(57) ABSTRACT

A method for monitoring changes in the boron concentration in the coolant of a reactor during a nuclear plant outage that applies temperature compensation to the source range detector output. The method then monitors the compensated output signal to identify changes in the detector count rate above a preselected value.

7 Claims, 2 Drawing Sheets

METHOD FOR MONITORING BORON DILUTION DURING A REACTOR OUTAGE

BACKGROUND

1. Field

This invention relates in general to monitoring the reactivity of a core of a nuclear reactor within the source range and more particularly to monitoring boron dilution during a reactor outage.

2. Related Art

In a pressurized water reactor power generating system, heat is generated within the core of a pressure vessel by a fission chain reaction occurring in a plurality of fuel rods supported within the core. The fuel rods are maintained in spaced relationship within fuel assemblies with the space between fuel rods forming coolant channels through which borated water flows. Hydrogen within the coolant water moderates the neutrons emitted from enriched uranium within the fuel rods to increase the number of nuclear reactions and thus increase the efficiency of the process. Control rod guide thimbles are interspersed within the fuel assemblies in place of fuel rod locations and serve to guide control rods which are operable to be inserted or withdrawn from the core. When inserted, the control rods absorb neutrons and thus reduce the number of nuclear reactions and the amount of heat generated within the core. Coolant flows through the assemblies out of the reactor to the tube side of steam generators where heat is transferred to water in the shell side of the steam generators at a lower pressure, which results in the generation of steam generally used to drive a turbine-generator set for the production of electricity. The coolant exiting the tube side of the steam generator is driven by a main coolant pump back to the reactor in a closed loop cycle to renew the process.

The power level of a nuclear reactor is generally divided into three ranges: the source or startup range, the intermediate range, and the power range. These three ranges can be further divided into six modes: mode one where the power is greater than five percent; mode two where the power is less than five percent; mode three, known as hot standby, where the temperature of the coolant is greater than 350°; mode four, also known as hot shutdown, where the temperature of the coolant is less than 350°; mode five, cold shutdown, where the temperature of the coolant is less than 200°; and mode six, refueling, where the temperature is less than 140°. The power level of the reactor is continuously monitored to assure safe operation. Such monitoring is typically conducted by means of neutron detectors placed outside and inside the reactor core for measuring the neutron flux of the reactor. Since the neutron flux in the reactor at any point is proportional to the fission rate, the neutron flux is also proportional to the power level.

Fission and ionization chambers have been used to measure flux in the source, intermediate and power range of a reactor. Typical fission and ionization chambers are capable of operating at all normal power levels, however, they are generally not sensitive enough to accurately detect low level neutron flux emitted in the source range. Thus, separate low level source range detectors are typically used to monitor neutron flux when the power level of the reactor is in the source range.

The fission reactions within the core occur when free neutrons at the proper energy level strike the atoms of the fissionable material contained within the fuel rods. The reactions result in the release of a large amount of heat energy which is extracted from the core in the reactor coolant and in the release of additional free neutrons which are available to produce more fission reactions. Some of these released neutrons escape the core or are absorbed by neutron absorbers, e.g., control rods, and therefore do not cause traditional fission reactions. By controlling the amount of neutron absorbing material present in the core, the rate of the fission process can be controlled. There are always random fission reactions occurring in the fissionable material, but when the core is shut down, the released neutrons are absorbed at such a high rate that a sustained series of reactions do not occur. By reducing the neutron absorbent material until the number of neutrons in a given generation equals the number of neutrons in the previous generation, the process becomes a self-sustaining chain reaction and the reactor is said to be "critical." When the reactor is critical, the neutron flux is six or so orders of magnitude higher than when the reactor is shut down. In some reactors, in order to accelerate the increase in neutron flux in the shutdown core to achieve practical transition intervals, an artificial neutron source is implanted in the reactor core among the fuel rods containing the fissionable material. This artificial neutron source creates a localized increase in the neutron flux to aid in bringing the reactor up to power.

In the absence of an artificial neutron source, the ratio of the number of free neutrons in one generation to those in the previous generation is referred to as the "neutron multiplication factor" ($K_{eff}$) and is used as a measure of the reactivity of the reactor. In other words, the measure of criticality for a nuclear core is $K_{eff}$, that is, the ratio of neutron production to total neutron loss attributable to both destruction and loss. When $K_{eff}$ is greater than one, more neutrons are being produced than are being destroyed. Similarly, when $K_{eff}$ is less than one, more neutrons are being destroyed than are being produced. When $K_{eff}$ is less than one, the reactor is referred to as being "subcritical."

During a refueling outage the reactor head is removed along with the upper internals structure to gain access to the fuel assemblies within the core. To provide such access, the control rods are removed with the upper internal structure, however, to maintain the fuel assemblies within the core subcritical with the control rods removed, the concentration of boron within the coolant within the core is increased. Monitoring the reactor coolant system boron concentrations during plant outages is a key aspect to verifying shutdown margin and preventing an inadvertent criticality. During the transition from mode six up to mode two, following a refueling outage, the plant will change boric acid concentration from approximately 2,300 ppm to 1,800 ppm. During this transition period in the outage, there are a large number of activities being performed which demand the attention of plant operators. Typically, shutdown margin is primarily monitored by periodic reactor coolant system boron concentration sampling and administratively locking out dilution sources to prevent inadvertent dilutions of boron in the reactor coolant system. Most plants also have boron dilution monitors in place that sample the output signals of the source range detectors for a statistically significant increase in count rates and provide an alarm based on a manually adjusted, preset increase in the count rate; e.g., a doubling in the count rate.

During a refueling outage at one commercial nuclear plant in May 2011, the reactor coolant system boron concentration unexpectedly decreased from 2,443 ppm to 1,483 ppm in 24 hours due to a leaking valve. The required shutdown boron concentration was 1,410 ppm. The source range detectors' output signals increased by a factor of three, but operations attributed this increase primarily to the concurrent reactor coolant system temperature increase. This utility had previously removed their secondary artificial neutron sources, which lower their source range detector count rate and make observing reactivity changes in a very subcritical state more difficult. While the plant was following the standard outage chemistry monitoring surveillance of taking samples every 24 hours, and the valves creating a dilution flow path were closed and locked out, but one leaked. A concurrent reactor coolant system temperature increase from about 325° F. to 475° F., while the dilution was occurring, masked the affect on the source range detectors and reduced the effectiveness of the manually adjusted, high flux at shutdown alarm.

Thus, a more sensitive detection system for identifying reactor coolant system boron concentration changes is desired.

Accordingly, it is an object of this invention to provide such a dynamic system that will continuously monitor boron concentration changes for changes that may not be readily detectable using the current methodology.

It is a further object of this invention to accurately monitor small changes in boron concentrations during operating modes six through two to protect a plant against an inadvertent criticality.

Further, is the object of this invention to provide such a system that is reliable enough to allow the elimination of the operating and core design constraints imposed by the current boron dilution accident analysis requirements.

SUMMARY

These and other objects are achieved employing a method for monitoring boron concentrations in a reactor coolant system during a nuclear plant outage that employs electrical outputs of existing instrumentation within the plant. The method monitors an output signal representative of a count rate of a source range neutron detector positioned outside of the reactor vessel within proximity of the core of the reactor, as a function of time, during the plant outage. The method also monitors a temperature of the coolant within the reactor coolant system as a function of time. The method further generates a compensation signal which is a function of the monitored temperature, that when combined with the count rate output signal compensates the count rate output signal for substantially any change in the count rate output signal resulting from a change in the temperature of the coolant. The method then applies the compensation signal to the count rate output signal to obtain a compensated count rate output signal and identifies a preselected increase in the compensated count rate output signal.

In a preferred embodiment, the compensation signal is defined as a downcomer, temperature attenuation factor (DTAF) given by the expression:

$$DTAF(T_1) = e^{-(p(T_1) - p(T_R))R}; \quad (1)$$

where the value of R is a function of distance between the source range detector and the reactor vessel and the effective macroscopic neutron removal cross section between the source range detector and the fuel assemblies on the core periphery and p is the change in density of the water inside the reactor vessel. A deviation in the compensated count rate output signal ($\Delta C_c(t)$) from a selected reference $\Delta C$ ($\Delta C_R$) is an indication that a reactivity change is happening or has happened and the value of $\Delta C_c(t)$ is given by the expression:

$$\Delta C_c(t) DTAF(t) - C_R. \quad (2)$$

Preferably, the application of error propagation techniques to determine the expected random fluctuations in $\Delta C_c$ from one monitored count rate output signal set to the next allows the expected range of random fluctuation in $\Delta C_c(\Delta CE)$ to be expressed substantially as:

$$\Delta C_E(t) \in 0 \pm 2\sigma_{CR}[1 + ]\frac{1}{DTAF(t)}; \quad (3)$$

where the value of $\sigma_{CR}$ is the measured mean deviation of significant population of source range count rate measurements obtained in an interval around time t; the value of C(t) is the mean value of the data used to determine $\sigma_{CR}$; and the number of count rate measurements used to determine $\sigma_{CR}$ is an operator addressable constant that is a function of the desired maximum value of $\sigma_{CR}$ needed to obtain a desired reactivity change detection sensitivity. In the foregoing embodiment, if $\Delta C(t)$ is outside an expected range of $\Delta C$ provided by the foregoing equation (3), the method identifies that a reactivity change is occurring or has occurred. Preferably, a selected number of consecutive samples of $\Delta C(t)$ are determined with a given fraction of the samples being outside the expected range of $\Delta C$ before identifying that a reactivity change is occurring. In one embodiment, the selected number of consecutive samples is approximately ten.

BRIEF DESCRIPTION OF THE DRAWINGS

A further understanding of the invention can be gained from the following description of the preferred embodiments when read in conjunction with the accompanying drawings in which.

DESCRIPTION OF THE PREFERRED EMBODIMENT

Figure 1:
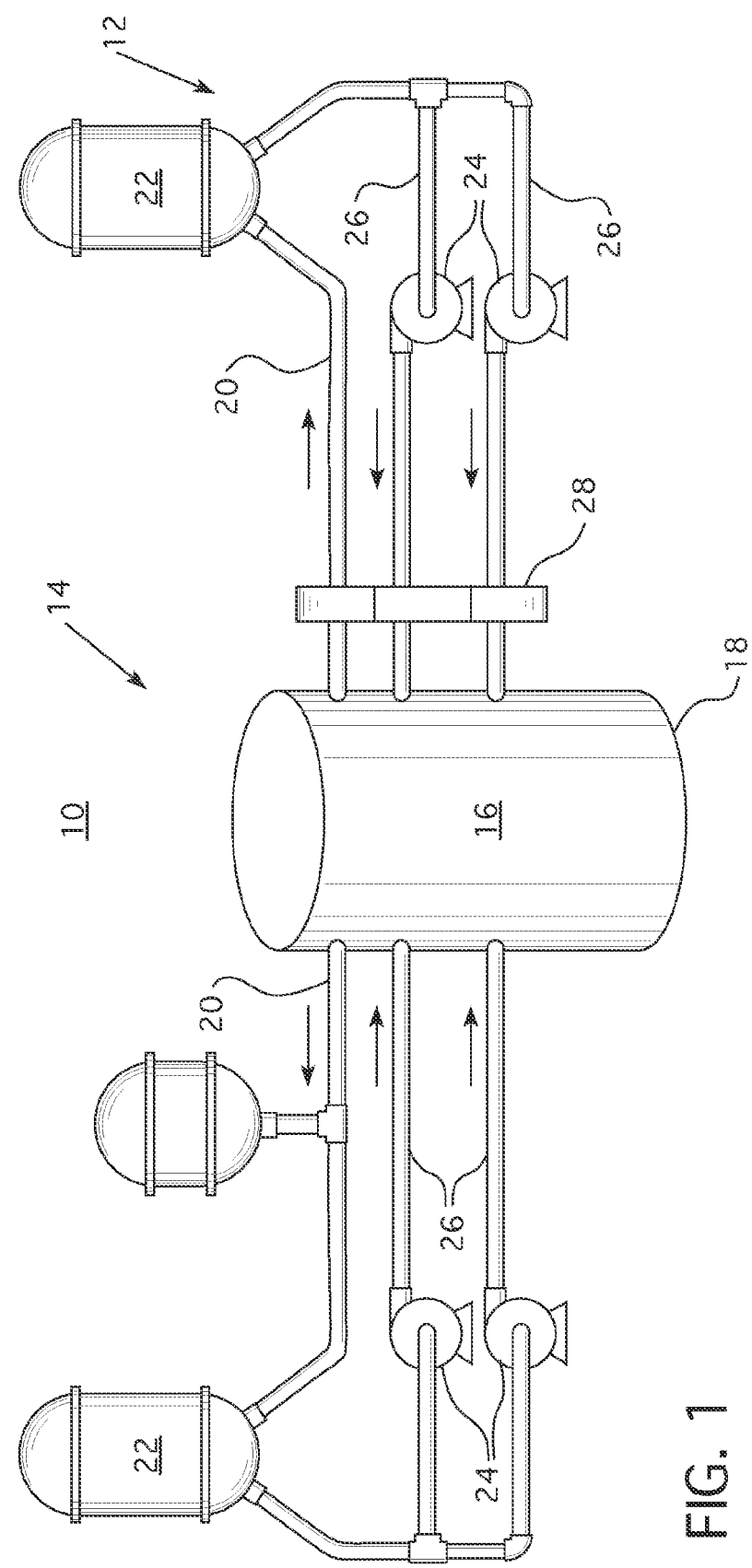
FIG. 1 is a schematic representation of a primary side of a nuclear power generating system.

FIG. 1 illustrates the primary side of a nuclear electric power generating plant 10 in which a nuclear steam supply system 12 supplies steam for driving a turbine-generator (not shown) to produce electric power. The nuclear steam supply system 12 has a pressurized water reactor 14 which includes a reactor core 16 housed within a pressure vessel 18. Fission reactions within the reactor core 16 generate heat, which is absorbed by a reactor coolant, like water, which is passed through the core. The heated coolant is circulated through hot leg piping 20 to a steam generator 22. Reactor coolant is returned to the reactor 14 from the steam generator 22 by a reactor coolant pump 24 through the cold leg piping 26. Typically, a pressurized water reactor has at least two and often three or four steam generators 22 each supplied with heated coolant through a hot leg 20, forming with the cold leg 26 and the reactor coolant pump 24, a primary loop. Each primary loop supplies steam to the turbine-generator. Two such loops are shown in FIG. 1.

Coolant returned to the reactor 14 flows downward through an annular downcomer and then upward through the core 16. The reactivity of the core and therefore the power output of the reactor 14 is controlled on a short term basis by control rods, which may be selectively inserted into the core. Long term reactivity is regulated through control of the concentration of a neutron moderator such as boron dissolved in the coolant. Regulation of the boron concentration effects reactivity uniformly throughout the core as the coolant circulates through the entire core. On the other hand, the control rods effect local reactivity and therefore, result in an asymmetry of the axial and radial power distribution within the core 16. Conditions within the core 16 are monitored by several different sensor systems. These include an excore detector system 28 which measures neutron flux escaping from the reactor 14. The excore detectors 28 includes source range detectors used when the reactor is shut down, intermediate range detectors used during startup and shutdown and power range detectors used when the reactor is above approximately five percent power. In-core detectors are also typically employed during power operation.

It is known to those skilled in the art that changes in the source range detector count rate ($\Delta C$) can be identified by corresponding changes in the core $K_{eff}$. In an ideal case the change in reactivity between a reference $K_{eff}$ ($K_R$) and another condition value of $K_{eff}$ ($K_1$) and time t is typically expressed as:

$$C_1(t) - C_R = \Delta C(t) = C_0 \left[ \frac{K_1(t) - K_R}{1 - K_1(t)} \right] \quad (4)$$

It has also been shown that changes in reactor coolant system temperature produces changes in the measured source range detector response due to the change in density (p) of the water inside the reactor vessel. The measured source range count rate at any time and corresponding reactor coolant system temperature ($T_1$) may be corrected to account for changes from a reference temperature ($T_R$) by applying a correction factor defined as the downcomer, temperature attenuation factor (DTAF) given by the expression:

$$DTAF(T_1) = e^{-(p(T_1) - p(T_R))R}. \quad (1)$$

The monitored reactor coolant system temperature may be taken from the cold leg, the hot leg or an average of the two. The value of R is a function of distance between the source range detector and the reactor vessel and the effective macroscopic neutron removal cross section between the source range detector and the fuel assemblies on the core periphery. R is determined either empirically from count rate measurements taken at different temperatures while holding core reactivity constant, or analytically using standard neutron transport methods. If the temperature inside the reactor vessel is changed with no corresponding significant change in core reactivity, the application of the DTAF to the measured count rate during the temperature change will serve to keep the corrected $\Delta C(t)$ essentially constant. The correction ensures that the reactor operators do not confuse a change in source range count rate caused by the reactor coolant system temperature change with a count rate change caused by reactivity changes such as those that would be seen if the reactor coolant system boron concentration was being changed.

Figure 2:
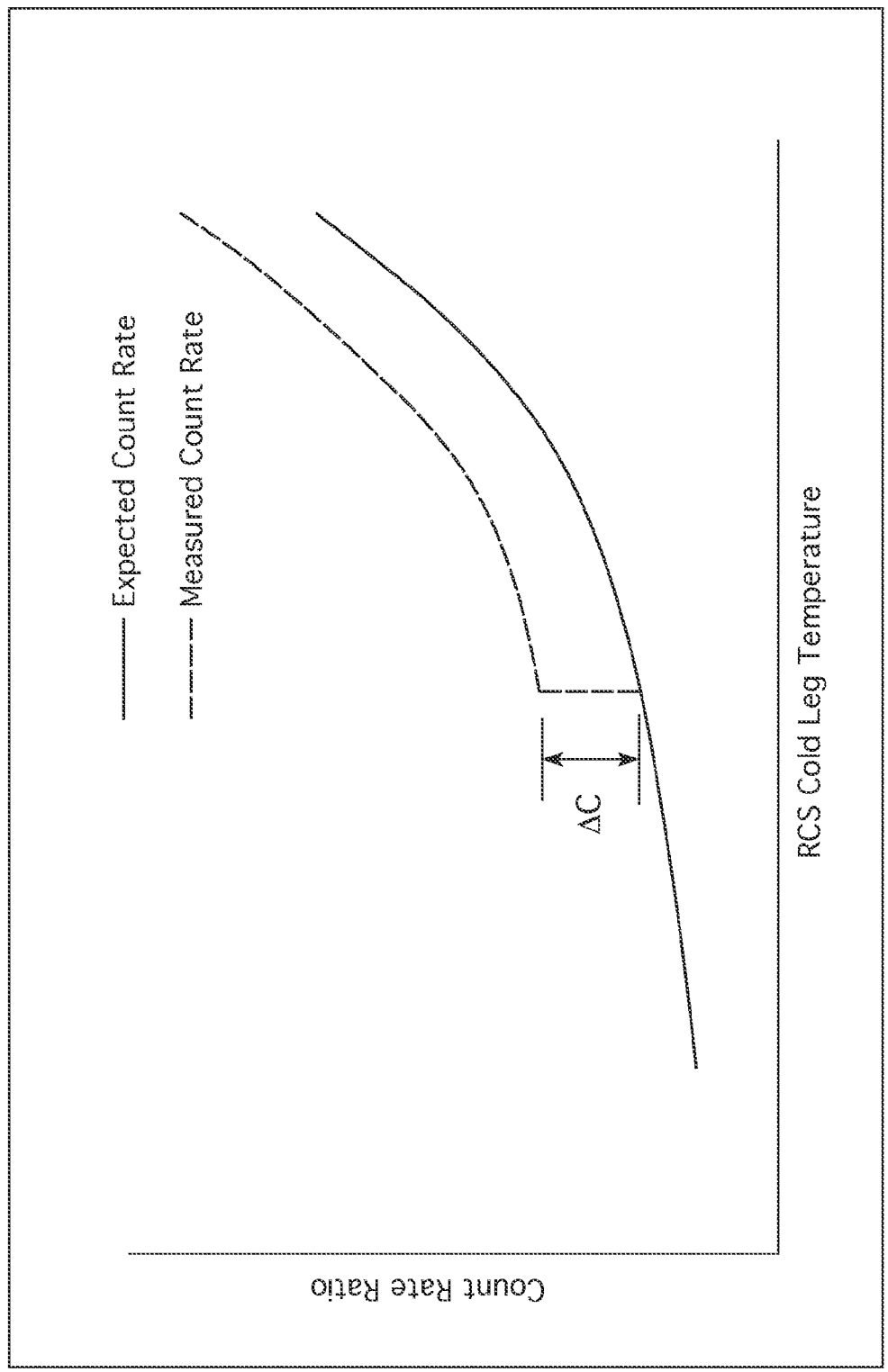
FIG. 2 is a graphical plot of the count rate ratio versus reactor coolant system cold leg temperature for the expected count rate and the measured count rate.

Deviation of the corrected measured value of $\Delta C(t)$ ($\Delta C_C(t)$) from a selected reference $\Delta C$ ($\Delta C_R$) is now an indication that a reactivity change is happening or has happened. This unexpected change in count rate is shown graphically as a function of reactor coolant system temperature in FIG. 2. The value of $\Delta C_C(t)$ is given by the expression:

$$\Delta C_c(t) DTAF(t) - C_R. \quad (2)$$

The process measurement and inherent random nature of measured source range detector signals will induce fluctuations in the measured value of $\Delta C$ at each time step, i.e., sampling These fluctuations will make the use of $\Delta C(t)$ for detecting small reactivity changes problematic. Application of error propagation techniques to determine the expected random fluctuations in $\Delta C_C$ from one count rate measurement set to the next allows the expected range of random fluctuation in $\Delta C_C$ ($\Delta C_E$) to be determined at a 95% confidence level by the expression:

$$\Delta C_E(t) \in 0 \pm 2\sigma_{CR}[1 + ]\frac{1}{DTAF(t)}. \quad (3)$$

The value of $\sigma_{RC}$ is the measured mean deviation of a significant population of source range count rate measures obtained in an interval around time t. The value of C(t) is the mean value of the data used to determine $\sigma_{CR}$. The number of count rate measurements used to determine $\sigma_{CR}$ is an operator addressable constant that is a function of the desired maximum value of $\sigma_{CR}$ needed to obtain a desired reactivity change detection sensitivity. If the measured $\Delta C_C$(t) is outside the expective range of $\Delta C$ provided by equation three, the operator can conclude that a reactivity change is occurring. In order to avoid false positive or negative indications, the use of a requirement for a number of consecutive cycles outside or inside the expected range is required before the status is set for display to the operator.

The steps of the preferred embodiment of the methodology of the invention claimed hereafter is as follows:

(a) obtain a set of source range detector count rate measurements;

(b) compute the mean value of the set;

(c) compute the mean deviation of the data set;

(d) repeat steps (a), (b) & (c) until a target mean deviation value is obtained;

(e) input the mean deviation value from step (d) as a reference value ($C_R$), into an alarm system for identifying unacceptable changes in the boron concentrations;

(f) obtain a new data set of source range detector measurements until the mean deviation of the new data set is no larger than the mean value obtained at step (d);

(g) compute the mean value of the data set used to complete step (f);

(h) compute the value of DTAF to be applied to the mean value from step (g) using the mean temperatures corresponding to the reference count rates and the count rates used to calculate the mean value from step (g);

(i) multiply the DTAF from step (h) times the mean count rate from step (g);

(j) subtract $C_R$ from the value obtained at step (i);

(k) determine whether the difference calculated in step (j) is outside an expected deviation range provided in equation three;

(l) if the difference from step (j) is inside the expected range, repeat steps (f) through (k) approximately ten or more times (if the difference is outside the expected range proceed to step 13);

(m) if at least nine of the measured difference values are within the expected range, set the reactivity change status output to a no alarm status;

(n) repeat steps (f) through (l) approximately ten or more times;

(o) if at least nine of the values obtained from step (13) are outside the expected range, set the reactivity change status output to "yes;" and (p) repeat steps (f) through (o) until the source range detectors are de-energized.

A new value of $C_R$ will be obtained and inputted into the system following the completion of all plant outage reactivity changes. It should be appreciated that the number of additional data collected and analyzed that is specified in steps (l) and (n) is a user adjustable input. Similarly, the number of measured difference values that have to be within or outside the expected range to set the reactivity status of the system set forth in steps (m) and (o) will depend upon the desired accuracy of the result and is user adjustable input.

While specific embodiments of the invention have been described in detail, it will be appreciated by those skilled in the art that various modifications and alternatives to those details could be developed in light of the overall teachings of the disclosure. Accordingly, the particular embodiments disclosed are meant to be illustrative only and not limiting as to the scope of the invention which is to be given the full breadth of the appended claims and any and all equivalents thereof.

What is claimed is:

1. A method for determining a change in boron concentrations in a reactor coolant system as a result of a reactivity change during a nuclear plant outage comprising the steps of:
   monitoring an output signal representative of a count rate of a source range neutron detector positioned outside of a reactor vessel within proximity of a core of a reactor, as a function of time, during a plant outage;
   monitoring a temperature of a coolant within the reactor coolant system as a function of time;
   generating a compensation signal which is a function of the monitored temperature, that when combined with the count rate output signal compensates the count rate output signal for substantially any change in the count rate output signal resulting from a change in the temperature of the coolant;
   applying the compensation signal to the count rate output signal to obtain a compensated count rate output signal; and
   identifying a preselected increase in the compensated count rate output signal as an indicia of a change in boron concentration.

2. The method of claim 1 wherein the compensation signal is defined as a Downcomer Temperature Attenuation Factor (DTAF) given by the expression:

$$DTAF(T_1) = e^{-(p(T_1)-p(T_R))R};$$

Where the value of R is a function of distance between the source range detector and the reactor vessel and the effective macroscopic neutron removal cross section between the source range detector and the fuel assemblies on the core periphery.

3. The method of claim 2 wherein a deviation in the compensated count rate output signal ($\Delta C_c(t)$) from a selected reference $\Delta C$ ($\Delta C_R$) is an indication that a reactivity change is happening or has happened and the value of $\Delta C_c(t)$ is given by the expression:

$$\Delta C_c(t) DTAF(t) - C_R.$$

4. The method of claim 3 wherein the application of error propagation techniques to determine the expected random fluctuations in $\Delta C_c$ from one monitored count rate output signal set to the next allows the expected range of random fluctuation in $\Delta C_c$ ($\Delta CE$) to be expressed substantially as:

$$\Delta C_E(t) \in 0 \pm 2\sigma_{CR}[1+]\frac{1}{DTAF(t)};$$

Where the value of $\sigma_{CR}$ is the measured mean deviation of significant population of source range count rate measurements obtained in an interval around time t; the value of C(t) is the mean value of the data used to determine $\sigma_{CR}$; and the number of count rate measurements used to determine $\sigma_{CR}$ is an operator addressable constant that is a function of the desired maximum value of $\sigma_{CR}$ needed to obtain a desired reactivity change detection sensitivity.

5. The method of claim 4 including the step of determining if $\Delta C(t)$ is outside an expected range of $\Delta C$ provided by the equation $$\Delta C_E(t) \in 0 \pm 2\sigma_{CR}[1+]\frac{1}{DTAF(t)};$$

and
   identifying that a reactivity change is occurring or has occurred.

6. The method of claim 5 wherein a selected number of consecutive samples of $\Delta C(t)$ are determined with a given fraction of the samples being outside the expected range of $\Delta C$ before identifying that a reactivity change is occurring.

7. The method of claim 6 wherein the selected number of consecutive samples is approximately ten.

* * * * *